United States Patent [19]

Bui et al.

[11] Patent Number: 4,911,172
[45] Date of Patent: Mar. 27, 1990

[54] PROBE TIP ULTRASONIC TRANSDUCERS AND METHOD OF MANUFACTURE

[75] Inventors: Tuan Bui, Lane Cove; Saad Nasr, Brighton Lesands, both of Australia

[73] Assignee: Telectronics Pacing Systems, Inc., Englewood, Colo.

[21] Appl. No.: 174,740

[22] Filed: Mar. 28, 1988

[51] Int. Cl.⁴ .................................................. A61B 8/12
[52] U.S. Cl. ............................. 128/662.06; 128/662.05
[58] Field of Search ....................... 128/662.05, 662.06; 73/622, 623

[56] References Cited

U.S. PATENT DOCUMENTS

| | | | |
|---|---|---|---|
| 3,938,502 | 2/1976 | Bonn | 128/662.06 |
| 4,407,294 | 10/1983 | Vilkomerson | 128/662.05 |
| 4,582,067 | 4/1986 | Silverstein et al. | 128/662.05 |
| 4,697,595 | 10/1987 | Breyer et al. | 128/662.06 |
| 4,794,931 | 1/1989 | Yoak | 128/662.06 X |

Primary Examiner—Francis Jaworski
Attorney, Agent, or Firm—Gottlieb, Rackman & Reisman

[57] ABSTRACT

An improved ultrasonic transducer for a catheter tip has a thin strip of piezoelectric polymer film formed into a spiral ring and adhesively mounted on the support structure near the catheter tip. Electrical connection between the back face of the film and the support structure negative electrode is via capacitive coupling. Connection to the front face of the film is via a wire connected to the positive electrode of the catheter. A further embodiment suitable for a needle transducer is formed by coating the tip with a solution of PVDF co-polymer to form the actual transducer.

5 Claims, 3 Drawing Sheets

PROBE TIP ULTRASONIC TRANSDUCERS AND METHOD OF MANUFACTURE

BACKGROUND AND PRIOR ART

This invention relates to the field of ultrasonic transducer for use with probes. Examples are transducers associated with catheter tips for use with cardiac pacing and electrophysiologic study leads that are implanted temporarily or permanently within a body, and needle tip transducers useful for biopsy and catheterization. The invention also relates to the probes themselves and methods for their manufacture.

External and implanted cardiac pacemakers are widely used to diagnose and treat a broad class of cardiac arrhythmias. The electrical pulses for heart stimulation are applied to the heart muscle via flexible leads with active electrodes on their tips. Electrical signals of the heart can be measured using the same technique with multipolar leads for electrophysiologic studies.

Cardiac catheterization requires the accurate positioning of a catheter within the heart. Positioning is commonly accomplished through the use of an x-ray system. Recently there has been interest in the use of two-dimensional ultrasonic echocardiography to localize the catheter tip. Usually an ultrasonic acoustic transducer is mounted at the tip of the catheter to allow location of catheter tip employing standard ultrasonic sensing equipment. Such equipment operates by employing a transducer to detect ultrasonic radiation emitted from the equipment and reflected from tissue under study. It is also known to emit ultrasonic energy from other sources and detect it at the equipment transducer. As the catheter is inserted into the patient's body and into the scan plane of an external ultrasound imaging probe, the ultrasound energy is detected by the catheter tip transducer. Based on the elapsed time between transmission of a pulse from the imaging probe and the reception of an echo by the catheter tip transducer, it is possible to calculate and display the exact position of the tip of the catheter on the display unit of the imaging probe.

A convenient way to ensure that the catheter tip transducer is omnidirectional is to use a tubular shaped transducer mounted on the wall and near the tip of a catheter. A tubular-shaped transducer has an omnidirectional radiation pattern in the plane perpendicular to the axis of the transducer. Piezoelectric polymer film is often used as transducer material because it is thin, flexible and can be made into complex shapes. Common types of piezoelectric film are PVDF or PVDF copolymer. Use of such films has, however, encountered manufacturing difficulties since the polymer film is difficult to roll into tubular form because of the small dimension of the film. Typically, the edge of the film tends to lift up. Further, it is difficult to ensure that the adhesive material is uniformly distributed between the catheter surface and the PVDF film.

In various biopsy and catheterization procedures, accurate localization of the tip of the biopsy needle or a catheter is required. A number of methods have been proposed that involve the use of ultrasound imaging for locating the tip.

Basically this requires mounting one or more transducers on the tip of the instrument. By using an ultrasound imaging probe, the patient's body is examined to locate the point of interest and guide the instrument tip to that position.

Jan Lesny and Joseph Aindow (UK Patent GB2 157 828 issued on Mar. 4, 1987), described a method to mount a transducer at the end of a needle tip. In this invention, a small PVDF element is mounted on the central conductor by means of a small dab of silver loaded epoxy. A thin film of varnish is then applied to the edge of the element to ensure electrical isolation of the front and back faces of the PVDF element. A thin film of gold is then sputtered over the entire outer surface of the needle to provide electrical conductivity. A protective layer of one or more metal layers is then electroplated over the sputtered layer.

There are several difficulties with this design. Firstly, the PVDF element mounted on the central conductor is very small (on the order of 100 micron), therefore it is very difficult to handle and position accurately on the tip of the needle. Secondly, it is very difficult to use a dab of silver loaded epoxy to connect to one electrode of the PVDF film (the back electrode) and at the same time ensure that the epoxy is not smeared or contact is made with the other electrode of the PVDF film (the front electrode). Contact with both the front and back electrodes by the silver loaded epoxy causes a short in the PVDF film and renders it useless. This is a severe problem because the PVDF film is very thin, in the order of 8–30 micron thick.

Vilkomerson (U.S. Pat. No. 4,407,294 issued Oct. 4, 1987) described a method to determine the location of a needle tip by mounting a number of hemispherical transducers on the opposite sides of the tip of an elongated stylet. Again, this technique is extremely difficult because of the need to mount the hemispherical transducers onto the tip of the stylet.

SUMMARY OF THE INVENTION

It is an object of this invention to provide a novel cardiac catheter in which the transducer completely encases the catheter core or the supporting structure of the catheter and a simplified method for its construction.

It is an object of the present invention to provide a convenient method to manufacture the transducer at the tip of a needle.

It is a further object of the present invention to provide a convenient method to manufacture the transducer at the tip of a catheter.

DETAILED DESCRIPTION OF A PREFERRED EMBODIMENT

Figure 1:
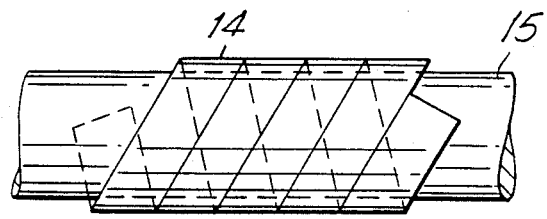
FIG. 1 is a view of a strip of PVDF wound on a forming rod.

In accordance with the principle of the present invention, a PVDF transducer is constructed. The process begins by cutting a piezoelectric film, preferably PVDF into an approximately 0.7–1 mm width strip. As shown in FIG. 1, the PVDF film strip 14 is spirally wound onto a forming rod 15. The strip 14 is clamped in place and heat treated at about 60°–80° C. to cause the piezoelectric film to retain its spiral form.

Figure 2:
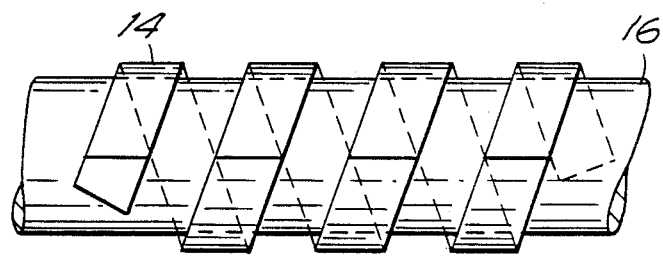
FIG. 2 is a view of strip of PVDF wound on a larger diameter rod and cut longitudinally.
Figure 3:
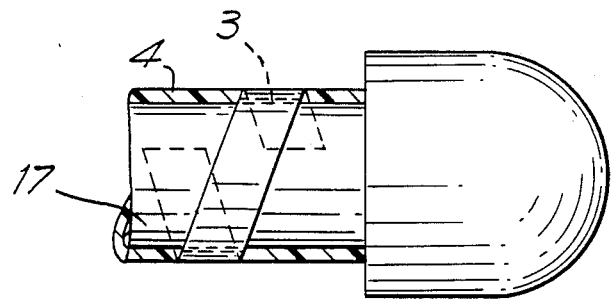
FIG. 3 shows the mounting of the PVDF film coil on the catheter tip.
Figure 4:
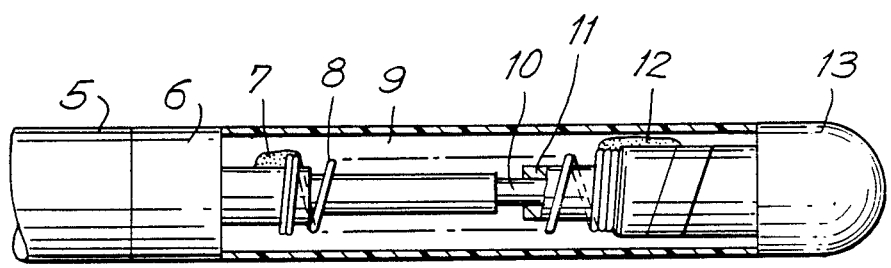
FIG. 4 shows a catheter attached to an ultrasonically visible tip.

As shown in FIG. 2, the preformed spiral film may be removed from the forming rod, and inserted over another, slightly larger in diameter rod 16. This rod may have the same diameter as the intended catheter tip onto which the film will be fit. The spiral is then clamped and cut longitudinally to produce single coil transducers.

The piezoelectric coil is mounted on the intended support 17 which has a diameter slightly larger than the forming rod. The film then fits tightly on the support. A low viscosity adhesive 3 is applied between the gap of the spiral ring to provide adhesion to the support rod. It should be understood that single or multicoil spiral film can be produced in this way and used.

Electrical connection to the inner surface of the spiral ring is accomplished via capacitive coupling through the adhesive layer 3. Electrical connection to the outer surface of the film is achieved by connecting a wire to the film using a conductive epoxy or another mechanical contact technique well known in the art.

The exposed surface of catheter tip adjacent to the mounted transducer is then coated with low viscosity insulator 4 to form an insulating film same thickness as the transducer. The catheter tip carrying the transducer is then connected to the main part of the catheter 5, for example by crimping 11 over lead 10 to make contact and attach the tip. The area of the crimp is then insulated with a low viscosity insulator. The top face of the transducer is then connected to the other (positive) electrode 6 of catheter via a previously inserted metal coil 8 using conductive epoxy 12 and 7 to make electrical contact and secure the coil to the tip 13 and the electrode 6 respectively.

This construction is then insulated by molding flexible ultrasonically transparent material, such as elastomer or any other, to form a tubular shell 9 in line with the outer surface of the main part of the catheter 5.

Figure 5:
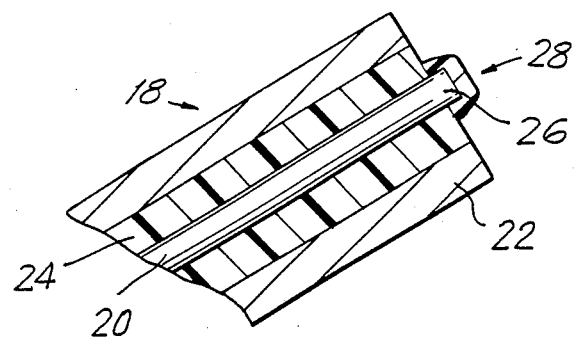
FIG. 5 shows a cross section of an improved needle tip transducer on a stylet.

As a further embodiment of the present invention there is disclosed an improvement in the manufacturing of the needle tip transducer. Basically, as shown in FIG. 5, a coaxial stylet 18 is constructed with the inner conductor 20 slightly protruded 26 from the outer conductor 22 and spaced therefrom by a coaxial insulator 24. The stylet is dipped in a solution of piezoelectric polymer such as PVDF co-polymer of VDF and TrFe in Methylethylketone solution (MTK). The MTK can be evaporated off and the P(VDF-TrFe) crystallized surface 28 formed on the surface of tip of the stylet.

There are various ways to control the thickness of the co-polymer layer 28. They are well known in the art. One method is to spin the needle at a high speed so that the centrifugal force results in a uniform layer on the tip of the needle.

There are certain advantages using this method.

Firstly, there is no need to use conductive adhesive to connect the film to the stylet. Electrical connection is achieved by capacitive coupling of the film to the inner conductor of the coaxial stylet. Secondly, the procedure can be performed quickly and does not require a high level of manual skill.

The front electrode can also be put on by conventional sputtering or vacuum deposition which are well known in the art. The transducer then can be poled by a corona discharge or other technique well known in the art (poling is used to make the polymer piezoelectric). A similar technique can be used to apply a transducer on the tip of a catheter.

The technique is not limited to the PVDF co-polymer but is applicable to all soluble piezoelectric polymers, and is not limited by the size and shape of the coaxial stylet.

Figure 6:
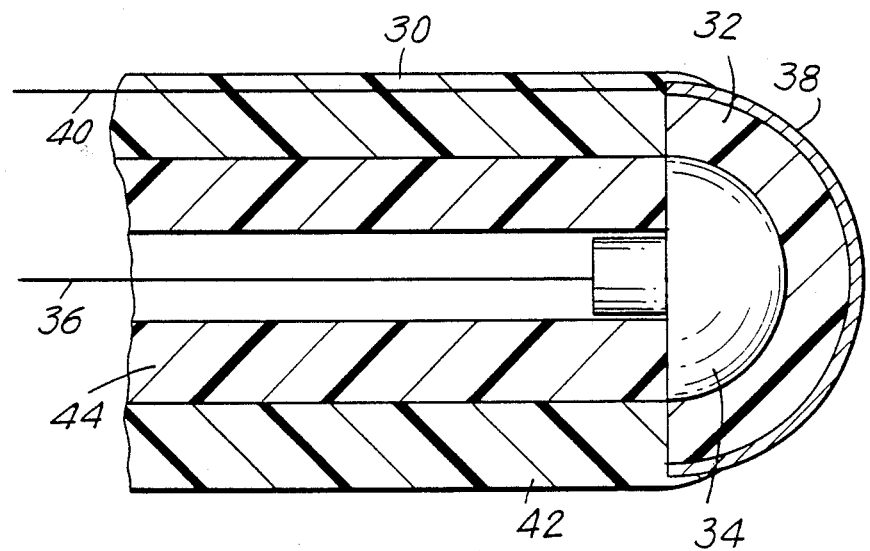
FIG. 6 shows a cross section of an improved catheter tip transducer.

Furthermore, the same principle can be applied to produce a transducer at the tip of a catheter 30 or an electrophysiological lead, as shown in FIG. 6. The tip of the lead 34 may be dipped into a solution of PVDF co-polymer and the polymer allowed to crystallize forming a PVDF copolymer layer 32. Electrical connection to the inner side of the transducer is via a central conductor 36 and capacitive coupling between the catheter tip 34 and the piezoelectric layer 32. The outer electrode 38 can be put on the surface of the piezoelectric film by conventional techniques well known in the art. Connection to the outer electrode is via connector 40. The connector is buried in a protective layer 42, which encloses catheter wall 44.

What is claimed is:

1. A biological probe enclosing first and second conductors and having a tip, the probe comprising an ultrasonic transducer formed from a piezoelectric material,
   said piezoelectric material having the form of a spiral ring about said probe tip, said spiral ring having inner and outer surfaces,
   said inner surface of said piezoelectric spiral ring being capacitively coupled to said first conductor,
   said outer surface of said piezoelectric spiral ring being electrically coupled to said second conductor.

2. The biological probe of claim 1 wherein said piezoelectric spiral ring is connected to said probe tip by a low viscosity adhesive and said inner surface of said piezoelectric spiral ring is capacitively coupled through said low viscosity adhesive to said first conductor.

3. The biological probe of claim 2 further comprising an insulator coating said tip and forming an insulating film having the same approximate thickness as said spiral ring.

4. The biological prove of claim 3 having a flexible lead portion with an outer generally cylindrical surface and further comprising an ultrasonically substantially transparent insulator forming a shell having an outer surface approximately in line with the outer surface of the probe.

5. A biological probe having a flexible lead portion with an outer generally cylindrical surface enclosing inner and outer coaxial conductors and a tip, the probe comprising an omnidirectional ultrasonic transducer formed from a piezoelectric material,
   said piezoelectric material having the form of a spiral ring of width approximately 0.7 to 1.0 mm wide about said probe tip and connected thereto by a low viscosity adhesive, said spiral ring having inner and outer surfaces,
   said inner surface of said piezoelectric spiral ring being capacitively coupled through said low viscosity adhesive to said inner coaxial conductor,
   said outer surface of said piezoelectric spiral ring being electrically coupled to said outer coaxial conductor,
   an insulator coating said tip and forming an insulating film having the same approximate thickness as said spiral ring,
   an ultrasonically substantially transparent insulator forming a tubular shell having an outer surface approximately in line with said outer surface of the probe.

* * * * *